(12) United States Patent
Hashmi et al.

(10) Patent No.: US 7,985,875 B2
(45) Date of Patent: Jul. 26, 2011

(54) PROCESS FOR PREPARING AROMATIC POLYCARBOXYLIC ACID BY LIQUID PHASE OXIDATION

(75) Inventors: Syed Azhar Hashmi, Riyadh (SA); Sulaiman Al-Luhaidan, Riyadh (SA)

(73) Assignee: Saudi Basic Industeies Corporation, Riyadh (SA)

( * ) Notice: Subject to any disclaimer, the term of this patent is extended or adjusted under 35 U.S.C. 154(b) by 15 days.

(21) Appl. No.: 12/448,386

(22) PCT Filed: Dec. 18, 2007

(86) PCT No.: PCT/EP2007/011213
§ 371 (c)(1), (2), (4) Date: Sep. 1, 2009

(87) PCT Pub. No.: WO2008/074497
PCT Pub. Date: Jun. 26, 2008

(65) Prior Publication Data
US 2009/0326265 A1    Dec. 31, 2009

(30) Foreign Application Priority Data
Dec. 21, 2006 (EP) .................................. 06026566

(51) Int. Cl.
*C07C 51/16* (2006.01)
*C07C 51/255* (2006.01)

(52) U.S. Cl. ....................................................... 562/416
(58) Field of Classification Search ........................ None
See application file for complete search history.

(56) References Cited

U.S. PATENT DOCUMENTS

| | | | |
|---|---|---|---|
| 2,833,816 A | 5/1958 | Saffer et al. | |
| 3,947,494 A | 3/1976 | Kuhlmann | |
| 6,355,835 B1 * | 3/2002 | Kulsrestha et al. | 562/417 |
| 2002/0055439 A1 * | 5/2002 | Palmer et al. | 507/200 |
| 2003/0181758 A1 | 9/2003 | Colborn et al. | |
| 2006/0004223 A1 | 1/2006 | Colborn et al. | |
| 2006/0004224 A1 | 1/2006 | Colborn et al. | |
| 2007/0161243 A1 * | 7/2007 | Mellies | 438/689 |
| 2010/0191010 A1 * | 7/2010 | Bosman et al. | 560/157 |

FOREIGN PATENT DOCUMENTS

| WO | WO 02/30862 | 4/2002 |
|---|---|---|
| WO | WO2005098920 | * 10/2005 |

OTHER PUBLICATIONS

M.Hronec, et al.:"Oxidation of p-xylene to terephthalic acid in benzoic acid and methyl ester of p-toluic acid." Collection Czechoslovak Chem Commun., v 52,1987 pp. 2241-2247.

G.A.Artamkina et al: "Oxidation of alkyl aromatic compounds with potassium permanganate under the conditions of interphase catalysis" J OrgChem USSR vol. 16 No. 4, 1980 p. 612-615.

* cited by examiner

*Primary Examiner* — Daniel Sullivan
*Assistant Examiner* — Jennifer C Sawyer

(57) ABSTRACT

The invention relates to a process for preparing an aromatic polycarboxylic acid by liquid phase oxidation of a di- or tri-substituted benzene or naphtalene compound, the process comprising a step of contacting the aromatic compound with an oxidant in the presence of a carboxylic acid solvent, a metal catalyst and a promoter in a reaction zone, wherein the promoter is an ionic liquid comprising an organic cation and a bromide or iodide anion. Advantages of this process include high conversion without severe corrosion problems otherwise associated with halogen-containing compounds as promoter. The process does not necessitate the use of special corrosion-resistant material or liners in the process equipment; thus offering savings on investment and maintenance costs and increasing plant reliability.

The process of the invention is especially suited for production of terephthalic acid from p-xylene.

13 Claims, No Drawings

PROCESS FOR PREPARING AROMATIC POLYCARBOXYLIC ACID BY LIQUID PHASE OXIDATION

The invention relates to a process for preparing an aromatic polycarboxylic acid by liquid phase oxidation of a benzene or naphtalene compound having two or three C1-C4 alkyl, hydroxyalkyl or formyl groups, the process comprising a step of contacting the compound with an oxygen-containing gas in the presence of a carboxylic acid solvent, a catalyst comprising at least one metal selected from the group consisting of cobalt, magnesium, chromium, copper, nickel, vanadium, iron, molybdenum, tin, cerium and zirconium, and a promoter in a reaction zone. More specifically, the invention relates to a process for preparing terephthalic acid comprising a step of oxidising in a reaction zone p-xylene with air or oxygen in the presence of acidic acid as solvent, a cobalt-manganese catalyst and a promoter.

Such a process is known from patent publication U.S. Pat. No. 6,355,835 B1, which describes a process for preparing a benzene dicarboxylic acid, for example terephthalic acid, by liquid phase oxidation of a xylene isomer, wherein the xylene is contacted with oxygen or air as oxidant in the presence of acetic acid as solvent, a cobalt salt as catalyst and an organic compound like acetaldehyde, tolualdehyde, butanone, or methyl ethyl ketone as promoter.

Terephthalic acid (TPA) and isopthalic acid (IPA), also known as 1,4- and 1,3-benzenedicarboxylic acid, are produced on large scale as key raw materials for various polymers; including thermoplastics like PET and PBT, and thermosetting polyester resins. Most of the commercially applied processes for making aromatic polycarboxylic acids like TPA are based on the technology originally described by U.S. Pat. No. 2,833,816. A soluble cobalt-manganese-bromine catalyst system forms the heart of these processes, yielding nearly quantitative oxidation of the starting xylene methyl groups. Acetic acid is generally used as solvent, and oxygen in compressed air is the oxidant, with reaction temperature in the range of 170-220° C. Various salts of cobalt and manganese can be used as catalyst, and the bromine source can be a.o. HBr, NaBr, ammoniumbromide or tetrabromoethane. The bromide is considered to act as a promoter, especially needed for activating the oxidation of the second (and further) methyl substituent. The oxidation reaction is performed in the liquid phase, but owing to the low solubility of the aromatic polycarboxylic acid in the solvent, most of it precipitates as it forms. This yields in fact a three-phase system: solid TPA crystals; solvent with dissolved starting aromatic compound, intermediate products, and some dissolved TPA; and vapour comprising nitrogen, acetic acid, water, and oxygen. The heat of reaction is removed by solvent evaporation. Typically, residence times of up to about 120 min. are used, resulting in over 98% of xylene being reacted and yield to TPA of over 95%. The oxidation of the methyl groups occurs in steps, with e.g. in case of p-xylene two intermediates being formed, i.e. p-toluic acid and 4-carboxybenzaldehyde (4-CBA; also called 4-formylbenzoic acid). 4-CBA is a troublesome compound, owing to its structural similarity to TPA, resulting in co-crystallisation with and in entrapment in the TPA. For making high molar mass linear polyester, monomers like terephthalic acid need to be of very high purity. Although the initial product obtained with a process as described above may contain >98% TPA, it is generally referred to as crude terephthalic acid (CTA). In order to make polymer grade TPA, commonly referred to as purified terephthalic acid (PTA), processes generally further comprise one or more reaction, purification and/or crystallisation steps.

The main disadvantage of these processes is that the bromine-based promoters in combination with the acetic acid solvent form a highly corrosive medium that requires the use of special and expensive metals like titanium as material of contact in major parts of the process equipment.

Many publications have addressed this problem, and various solutions have been proposed. GB 2000493 A, for example, describes a process comprising specific washing and separation steps, such that a reduced number of equipment parts need to be made from bromide-resistant material. U.S. Pat. No. 3,299,125 discloses a combination of cobalt and zirconium as catalyst, which would allow lower reaction temperatures, and thus milder conditions; but resulting in relatively low conversion at extended reaction times. In U.S. Pat. No. 6,153,790 also a process is described that applies a cobalt-zirconium catalyst, which process would not require the presence of a bromide promoter.

The process as described in U.S. Pat. No. 6,355,835 B1 does not apply a bromine-based promoter, but requires the use of high amounts of catalyst; the cobalt salt catalyst is applied at 5 to 25 mole % based on aromatic compound (xylene). A further drawback of this known process is that the organic promoters used may be oxidized under the applied reaction conditions, further complicating subsequent purification and recycling steps.

There is thus a need in industry for a process for preparing an aromatic polycarboxylic acid by liquid phase oxidation of an aromatic compound substituted by two or three alkyl, hydroxyalkyl or formyl groups, with an oxygen-containing gas in the presence of a carboxylic acid solvent, a metal catalyst and a promoter, which process does not use a highly corrosive medium, shows high conversion, and easy separation and recycling steps.

The object of the invention is therefore to provide such an improved process.

This object is achieved according to the invention with a process wherein the promoter is an ionic liquid comprising an organic cation and a bromide or iodide anion.

Surprisingly, the process as defined by claim 1 allows preparation of an aromatic polycarboxylic acid by liquid phase oxidation of a substituted benzene or naphtalene compound with an oxygen-containing gas in the presence of a carboxylic acid solvent, a metal catalyst and a bromide- or iodide-containing promoter with high conversion and favourable reaction rate, and without serious corrosion problems that are normally associated with using a halogen-containing compound as promoter. The process does not necessitate the use of highly corrosion-resistant materials or liners in the process equipment; thus offering savings on investment and maintenance costs and increasing plant reliability.

It is true that patent publication US 2004/0015009 A1 already disclosed a process wherein an ionic liquid was used in the oxidation of an aromatic compound with two alkyl-substituents, but in this process the ionic liquid is used as the solvent and preferably contains a sulphur-containing anion, like methanesulfonate. In addition, conversion was relatively low even after prolonged time.

Use of an ionic liquid with an organic cation and a bromide or iodide anion as promoter in the process according to the invention also enables the subsequent oxidation of the second substituent of the aromatic compound can be performed under the same reaction conditions as for the first substituent. A further advantage of the process according to the invention is that the ionic liquid can be easily and completely separated with other components from the solid polycarboxylic acid reaction product, and be recycled. Furthermore, no impurities like halogenated aromatic products were formed in detectable amounts, and no hazardous products like methyl bromide could be found in vent gases exiting the reactor.

The invention relates to a process for preparing an aromatic polycarboxylic acid by liquid phase oxidation of a benzene or naphtalene compound substituted by two or three alkyl, hydroxyalkyl or formyl groups having 1-4 carbon atoms. Particularly suitable alkyl groups are methyl, ethyl, and isopropyl groups; suitable hydroxyalkyl groups are hydroxymethyl and hydroxyethyl groups. The two or three of such groups present on the aromatic nucleus of the compound can be the same or different, to result in a bi- or tricarboxylic acid, respectively. Preferably, the aromatic compound has two methyl substituents. Examples of suitable compounds to be oxidised are o-, m-, and p-xylene, bishydroxymethylbenzenes, and 2,6-dimethylnaphthalene. Suitable compounds also include those which are already partially oxidised to carboxylic acids and their corresponding esters, for example p-toluic acid, methyl p-toluate and p-carboxyaldehyde.

Preferably, the process according to the invention relates to preparing terephthalic acid or isophthalic acid from p-xylene or m-xylene, respectively.

The carboxylic acid solvent that is used in the process according to the invention is a solvent for the starting substituted aromatic compound, and is substantially unaffected under the oxidation reaction conditions. Suitable carboxylic acids include lower aliphatic monocarboxylic acids having 2-8 carbon atoms, and benzoic acid. More preferably, a saturated aliphatic carboxylic acid with 2-4 carbon atoms and without hydrogen atoms at a tertiary carbon atom is used. Most preferably, acetic acid is used as solvent. The solvent may further comprise some water. The amount of solvent that is used is not critical, but preferably the ratio of solvent to aromatic compound is in the range of 3:1 to 15:1.

In the process of the invention a catalyst comprising at least one metal selected from the group consisting of cobalt, magnesium, chromium, copper, nickel, vanadium, iron, molybdenum, tin, cerium and zirconium is used, as described in earlier publications. These metals that have a variable valency can be used in the form of an inorganic or organic salt. Preferably an organic salt, more preferably a lower carboxylic acid salt is used, like a metal acetate. Preferably, a cobalt salt is used as catalyst, more preferably in combination with a manganese, cerium and/or zirconium salt. A catalyst comprising a combination of cobalt and manganese is most preferred, in view of its good activity and stability.

Preferably, the catalyst further contains an alkali metal, as this reduces the level of impurities, for example of p-toluic acid and 4-CBA in case of p-xylene oxidation. The alkali metal is preferably added in the form of a salt, as described above for the other metal component. More preferable, the catalyst further comprises potassium or cesium, most preferably a cesium salt.

The amount of catalyst that is used in the process according to the invention may vary widely, for example from several ppm to some %. In case cobalt and manganese are used as catalyst, their concentrations preferably are in the range of 10 to 10000 ppm and 20 to 20000 ppm, respectively (based on mass of solvent). More preferably, cobalt and manganese concentrations are in the range of 100 to 1000 ppm and 500 to 2000 ppm, respectively. The ratio of cobalt to manganese may vary widely, for example from 5/1 to 1/25, but is preferably from 2/1 to 1/15, more preferable from 1 to 1/10, or even about 1/5.

The process according to the invention for preparing an aromatic polycarboxylic acid comprises a step of contacting a substituted aromatic compound with an oxygen-containing gas as oxidant. Any oxygen-containing gas can be applied, like molecular oxygen, air or any other gas mixture comprising oxygen, e.g. nitrogen or carbon dioxide. In a preferred way of performing the process according to the invention the oxygen-containing gas comprises 4-50 vol % of carbon dioxide, preferably 10-25 vol %. This further reduces reaction time and side-reactions. The ratio of total amount of oxygen to the substituted aromatic compound is depending on the number of substituents to be oxidised. Preferably, oxygen is used in excess; for example the molar ratio of oxygen to aromatic compound is from 3 to 500, more preferably from 5 to 100.

The process according to the invention for preparing an aromatic polycarboxylic acid comprises a step of contacting a substituted aromatic compound with an oxidant in the liquid phase in a reaction zone. The liquid phase comprises the solvent, dissolved reactants, catalyst, promoter, etc. The applied reaction conditions, temperature and pressure, in the reaction zone are such that the liquid phase is maintained, and that the desired reaction occurs to obtain a desired conversion, yet not such that substantial evaporation or undesirable side-reactions occur. Generally, suitable temperatures are in the range 150-250° C., preferably in the range 185-225° C., and suitable pressure is in the range 1.5-2.5 MPa, preferably 1.8-2.2 MPa; as this results in the desired product at high conversions at a residence time on the order of 60 to 120 min.

The reaction zone in the process according to the invention can include one or more reactors as known to the skilled man, for example a stirred tank reactor that may be operated in a continuous or batch-wise way. It is an advantage of the present invention, that such reactor, and subsequent equipment parts, need not be made of a special bromide-resistant material, like titanium. Examples of suitable materials for such a reactor include metal alloys such as NiCrMo-alloys available as e.g. Hastealloy-C.

The invention relates to a process for preparing an aromatic polycarboxylic acid by liquid phase oxidation of a substituted aromatic compound, applying a metal catalyst and an ionic liquid comprising an organic cation and a bromide or iodide anion as promoter. An ionic liquid is defined herein as a compound that contains essentially only ions and has a melting point of below 200° C., being liquid at the applied conditions; in analogy with the definition given at http://www.chemsoc.org/ExemplarChem/entries/2004/bristol_vickery/ionic_liquids.htm. Ionic liquids generally are of low viscosity, are non-volatile, and inherently conductive. It is known that, as in conventional organic solvents, many kinds of chemical reactions occur in ionic liquids; and much research is being directed to their use as solvents in 'green chemistry' and biocatalysis. The properties of an ionic liquid may be tuned by choosing specific combinations of cations and anions.

The ionic liquid that is used as promoter in the process according to the invention comprises an organic cation in combination with a bromide or iodide anion. Preferably, the ionic liquid substantially consists of these types of cations and anions.

The organic cation may be of different structures, but preferably, the organic cation is a quaternary nitrogen-containing group. Suitable examples thereof include cyclic and aliphatic quaternary nitrogen-containing cations. Preferred cations are 1-alkylpyridinium or 1,3-dialkylimidazolium, wherein the alkyl groups can be linear or branched alkyls. Preferred alkyl groups contain 1-5, more preferably 1-3 carbon atoms. Advantages hereof include good stability, and good solubility in the reaction mixture.

The anion of the ionic liquid can be a bromide or iodide ion, but preferably the anion is a bromide ion because this results in high activity and selectivity as promoter in the process according to the invention. A preferred compound is 1-ethyl-3-methylimidazolium bromide, which provides a favourable combination of solubility, activity and stability.

The ionic liquid promoter in the process according to the invention can be used at relatively low concentration to obtain the desired effect. A suitable concentration range for the ionic liquid is from about 10 to about 50000 ppm (based on solvent), preferably the concentration is in the range 10-1000 ppm.

The ionic liquid comprising an organic cation and a bromide or iodide anion shows such activity as promoter, that no other promoter, like another bromine-containing compound, needs to be added in the process according to the invention. The reaction conditions for oxidising the second substituent (and optionally the third substituent) of the aromatic compound can be maintained as used for oxidising the first substituent (e.g. methyl groups). The ionic liquid promoter is not consumed in the reaction, and can be separated and re-used repeatedly.

In a preferred embodiment of the invention, the process concerns preparing terephthalic acid comprising a step of oxidising in a reaction zone p-xylene with air or oxygen in the presence of acidic acid as solvent, a cobalt-manganese catalyst and an ionic liquid containing a quaternary nitrogen-containing cation and a bromide anion as promoter. Further preferred conditions and embodiments of this process are analogous to those discussed in the above.

The process according to the invention may further comprise additional steps to isolate and purify the aromatic polycarboxylic acid, for example terephthalic acid, as obtained by the process as described above. Such processing steps are well known to the skilled person, and have been described in general literature, for example in relevant chapters of Ullmann's Encyclopaedia of Industrial Chemistry (e.g. as available via http://www.mrw.interscience.wiley.com/ueic/articles/a26_193/sect3-fs.html), and in above-cited patent publications, and literature references cited therein; especially for producing TPA and IPA, and for transferring crude terephthalic acid (CTA) into purified terepthalic acid (PTA). Such further processing steps may include isolation steps like filtration or centrifugation, washing steps, secondary reaction steps like hydrogenation or post-oxidation, and re-crystallisation and drying steps.

The invention will be further elucidated with reference to the following non-limiting experiments.

EXAMPLE 1

The experimental set-up includes a 1000 ml continuous stirred tank reactor, provided with mechanical stirrers, a gas delivery tube, a reflux condenser, a thermocouple, and a rupture disc. The reactor is heated by circulating hot oil from a temperature controlled oil bath. The exit gases are passed through a trap for further analyses. The reactor and other relevant equipment are made from Hastealloy C.

In this experiment p-xylene was oxidised with air as oxidant, using acetic acid as solvent, a combination of cobalt acetate tetrahydrate and manganese acetate tetrahydrate as catalyst, and 1-ethyl-3-methylimidazolium bromide as promoter.

The following experimental procedure was applied:
a) Perform a leak test by filling the reactor with nitrogen at 2.0 MPa for 30 min and check for leaks;
b) Charge 40 g of p-xylene to the reactor using a dosing pump at rate of 5 ml/min;
c) Charge 200 g of acetic acid to the reactor at rate of 10 ml/min;
d) Charge 10 g of catalyst and promoter solution [having $Co^{+2}$ concentration of 0.02 wt % (on solvent), $Co^{+2}/Mn^{+2}$ mass ratio of 1/5, and $Br^-/(Co^{+2}+Mn^{+2})$ ratio of 1.0/1.0] to the reactor at a rate of 1.0 ml/min;
e) Start the agitator slowly and set at 100-150 rpm;
f) Set the condenser temperature at 85° C. by circulating the hot oil from the bath;
g) Inject nitrogen at flow rate of 50 ml/hr and maintain reactor pressure at 1.8 MPa;
h) Heat the reactor to 215° C. by circulating hot oil from the bath and maintain pressure of 1.8 MPa with a pressure control valve;
i) After temperature has reached 215° C. close nitrogen line and inject air at 1.8 MPa, at a flow rate of 50 ml/hr;
j) Check the $O_2$ and $CO_2$ concentration in the off-gas with online gas analyzers; adjust air flow rate or temperature such that $[O_2]$ is in the range of 2.0-2.5 vol % and $[CO_2]$ is 1.3-1.5 vol %;
k) Continue the reaction for 120 min, and maintain the reactor temperature between 215-220° C. and pressure 1.8-1.9 MPa (monitor temperature and pressure continuously);
l) Record the temperature and control the exothermicity of reaction; stop air flow if reactor temperature increase above 225° C.;
m) After 120 minutes start cooling the reactor down to 20° C. by lowering hot oil bath temperature;
n) Vent the gases slowly by opening valve;
o) Remove the slurry product by opening bottom drain valve and collect it in a glass beaker;
p) Filter using buchner funnel and separate the solid CTA product and mother liquor at room temperature in hood;
q) Dry wet cake at 90° C. in oven for 2 hours;
r) Sample product and mother liquor for analysis.

The conversion of p-xylene was found to be virtually 100%. Gas chromatography on exit gas showed no detectable methylbromide. A further qualitative experiment was performed by passing the vent gases through silver nitrate solution; up on which no change in solution occurred, indicating that presumably no methylbromide was formed. In Table 1 the analyses results of the recovered solid product as determined by HPLC are given. HMWC means higher molecular weights compounds.

From the observation that no methylbromide nor brominated by products were found, it can be concluded that the bromide remains bounded in the ionic liquid compound, and does not form bromine-containing compounds that can cause corrosion. In addition the ionic liquid can be separated from the solid product stream, such that no bromine-containing compounds will be present in the product stream.

EXAMPLE 2

The procedure as described for Example 1 was repeated, but additionally cesium acetate was added, in such amount that $Br^-/Cs^+$ molar ratio was 1. The results on the recovered TPA product are depicted in Table 1, and demonstrate that addition of an alkali metal like cesium further improves catalyst performance; e.g. reduces the level of undesirable impurities.

Comparative Experiment A

The experiment of Example 1 was repeated, but now a conventional Co-based catalyst was used, with manganese bromide as promoter.

In the gas exiting the reactor traces of methylbromide were detected. The HPLC data on recovered solid product, shown In Table 1, clearly show that impurities like brominated aromatic products have been formed.

Such presence of bromide was not detected in the CTA prepared using an ionic liquid promoter; showing that the separation of the bromide containing ionic liquid from the product mixture is easy and complete. It is known that the prior art process with bromine compounds in the reaction medium causes metal corrosion up on prolonged exposure to such medium.

Comparative Experiment B

Example 2 was repeated, but now 1-butyl-3-methylimidazolium bromotrichloroaluminate was used as promoter. The conversion of p-xylene was found to be <50% as determined by GC, demonstrating the advantageous effect of a halogen anion in the ionic liquid.

TABLE 1

| Component | Unit | Example 1 | Example 2 | CE A |
|---|---|---|---|---|
| Terephthalic acid | % | 95.6 | 95.8 | 94.7 |
| P-toluic acid | % | 0.7 | 0.6 | 0.5 |
| 4-CBA | % | 2.2 | 1.4 | 2.8 |
| HMWC | % | 0.42 | 0.62 | 0.80 |
| Br-TA | % | 0.0 | 0.0 | 0.12 |
| Others | % | 0.35 | 0.85 | 0.65 |
| Cobalt | ppm | 3.8 | 1.6 | 1.8 |
| Manganese | ppm | 6.9 | 2.8 | 1.6 |
| Cesium | ppm | 0.0 | 1.2 | 0.0 |
| Bromide | ppm | 0.0 | 0.0 | 1.2 |
| Acid No. | KOH mg/g | 674.56 | 674.70 | 674.92 |
| Moisture | % | 0.26 | 0.18 | 0.14 |

The invention claimed is:

1. A process for preparing an aromatic polycarboxylic acid by liquid phase oxidation comprising contacting a benzene or naphthalene compound having two or three C1-C4 alkyl, hydroxyalkyl or formyl groups with an oxygen-containing gas in the presence of a carboxylic acid solvent, a catalyst comprising at least one metal selected from the group consisting of cobalt, magnesium, chromium, copper, nickel, vanadium, iron, molybdenum, tin, cerium and zirconium, and a promoter in a reaction zone, the promoter is an ionic liquid comprising an organic cation selected from the group consisting of 1-alkylpyridinium and 1,3-dialkylimidazolium and an anion consisting essentially of bromide or iodide and said ionic liquid having a melting point of below 200° C.

2. A process for preparing terephthalic acid or isophthalic acid by liquid phase oxidation comprising contacting p-xylene or m-xylene with an oxygen-containing gas in the presence of a carboxylic acid solvent, a catalyst comprising at least one metal selected from the group consisting of cobalt, magnesium, chromium, copper, nickel, vanadium, iron, molybdenum, tin, cerium and zirconium, and a promoter in a reaction zone, wherein the promoter is an ionic liquid comprising an organic cation selected from the group consisting of 1-alkylpyridinium and 1,3-dialkylimidazolium and a bromide or iodide anion and having a melting point of below 200° C.

3. The process according to claim 1, wherein the solvent is acetic acid.

4. The process according to claim 1, wherein the catalyst comprises cobalt and manganese.

5. The process according to claim 1, wherein the catalyst further comprises an alkali metal.

6. The process according to claim 1, wherein the oxygen-containing gas is oxygen or air.

7. The process according to claim 1, wherein the process further comprises a temperature of 150-250° C. and a pressure of 1.5-2.5 MPa in the reaction zone.

8. The process according to claim 1, wherein the anion is bromide.

9. The process according to claim 1, wherein the promoter is 1-ethyl-3-methylimidazolium bromide.

10. The process according to claim 1, wherein the promoter is present in a concentration of 10-1000 ppm (based on solvent).

11. A process for preparing terephthalic acid comprising in a reaction zone p-xylene with air in the presence of acetic acid as solvent, a cobalt-manganese catalyst and an ionic liquid comprising an organic cation selected from the group consisting of 1-alkylpyridinium and 1,3-dialkylimidazolium and a bromide anion as promoter, at a temperature of 150-250° C. and a pressure of 1.5-2.5 MPa.

12. The process according to claim 11, wherein the catalyst further comprises an alkali salt.

13. The process according to claim 11, wherein the promoter is 1-ethyl-3-methylimidazolium bromide, present in a concentration of 10-1000 ppm (based on solvent).

* * * * *